United States Patent [19]
Wong et al.

[11] Patent Number: 5,603,954
[45] Date of Patent: Feb. 18, 1997

[54] PENTOXIFYLLINE THERAPY AND METHOD OF USE

[75] Inventors: Patrick S. L. Wong, Palo Alto; George V. Guittard, Cupertino; Atul D. Ayer, Palo Alto, all of Calif.

[73] Assignee: ALZA Corporation, Palo Alto, Calif.

[21] Appl. No.: 449,621

[22] Filed: May 24, 1995

Related U.S. Application Data

[62] Division of Ser. No. 183,007, Jan. 18, 1994, Pat. No. 5,532,003.

[51] Int. Cl.$^6$ ........................................... A61K 9/22
[52] U.S. Cl. ........................ 424/473; 424/482; 424/489
[58] Field of Search ................................ 424/473, 482, 424/489

[56] References Cited

U.S. PATENT DOCUMENTS

| | | | |
|---|---|---|---|
| 2,798,053 | 7/1957 | Brown | 260/2.2 |
| 2,799,241 | 7/1957 | Wurster | 118/124 |
| 2,909,462 | 10/1959 | Warfield et al. | 167/56 |
| 3,133,132 | 5/1964 | Loeb et al. | 264/49 |
| 3,173,876 | 3/1965 | Zobrist | 252/137 |
| 3,276,586 | 10/1966 | Rosaen | 210/90 |
| 3,422,107 | 1/1969 | Mohler et al. | 260/256 |
| 3,541,005 | 11/1970 | Strathmann et al. | 210/19 |
| 3,541,006 | 11/1970 | Bixler et al. | 210/23 |
| 3,546,142 | 12/1970 | Michaels et al. | 260/2.1 |
| 3,825,069 | 7/1974 | Norton et al. | 166/305 R |
| 3,845,770 | 11/1974 | Theeuwes et al. | 128/260 |
| 3,916,899 | 11/1975 | Theeuwes et al. | 128/260 |
| 4,063,064 | 12/1977 | Saunders et al. | 219/121 L |
| 4,088,864 | 5/1978 | Theeuwes et al. | 219/121 LM |
| 4,160,020 | 7/1979 | Ayer et al. | 424/15 |
| 4,200,098 | 4/1980 | Ayer et al. | 128/260 |
| 4,248,857 | 2/1981 | DeNeale et al. | 424/21 |
| 4,285,987 | 8/1981 | Ayer et al. | 427/3 |
| 4,327,725 | 5/1982 | Cortese et al. | 128/260 |
| 4,612,008 | 9/1986 | Wong et al. | 604/892 |
| 4,765,989 | 8/1988 | Wong et al. | 424/473 |
| 4,783,337 | 11/1988 | Wong et al. | 424/468 |

OTHER PUBLICATIONS

Physicians' Desk Reference, 47th Ed., 1993, pp. 1125–1126.
The Merck Index, 11th Ed., 1989, p. 1131.
The Pharmacological Basis of Therapeutics, 8th Ed., 1990, p. 628.
Journ. Am. Phar. Assoc., Sci. Ed., vol. 48, pp. 451–454 (1959).
Journ. Am. Phar. Assoc., Sci. Ed., vol. 49, pp. 82–84 (1960).
Modern Plastics Encyclopedia, vol. 46, pp. 62–70 (1969).
Remington's Pharmaceutical Sciences, 14th Ed., pp. 1626–1678 (1970).
Physicians's Desk Reference, 43rd Ed., 1989 pp. 1029–1030.
Grant & Hackh's Chemical Dictionary, 5th Ed. 1989 p. 461.

*Primary Examiner*—D. Gabrielle Phelan
*Attorney, Agent, or Firm*—Paul L. Sabatine; Mary Ann Dillahunty; Felissa H. Cagan

[57] ABSTRACT

A dosage form is disclosed for delivering pentoxifylline to a patient in need of pentoxifylline therapy. A method is discussed for delivery pentoxifylline to a patient at a dosage form controlled rate over an extended period of time.

7 Claims, 3 Drawing Sheets

PENTOXIFYLLINE THERAPY AND METHOD OF USE

This application is a division of application Ser. No. 08/183,007, now U.S. Pat. No. 5,532,003, filed Jan. 18, 1994, and benefit of the filing date of said earlier filed application is claimed under 35 U.S.C. § 120.

FIELD OF THE INVENTION

This invention pertains to pentoxifylline therapy. More particularly, the invention relates to a dosage form that provides a controlled-continuous delivery of pentoxifylline over an extended period of time. The invention concerns also a method for administering to a patient pentoxifylline for the treatment of intermittent claudication consisting of occlusive arterial disease. The method comprises administering to a patient a dosage form that comprises pentoxifylline that is delivered in a therapeutically controlled-rate over an extended time for the intended therapy.

BACKGROUND OF THE INVENTION

The drug pentoxifylline is indicated for improving the flow properties of blood by decreasing its viscosity. For patients with chronic peripheral arterial disease, the administration of pentoxifylline increases the blood flow to the affected microcirculation and enhances tissue oxygenation. In therapy, tissue oxygen levels are increased by administering therapeutic doses of pentoxifylline to patients with peripheral arterial disease. The drug pentoxifylline is used for the treatment of claudication as accompanied by chronic occlusive arterial disease.

A critical need exists for a dosage form for the controlled-rate administration of pentoxifylline, which drug is administered presently in conventional pharmaceutical forms, such as tablets and capsules. The conventional forms deliver their drug by dumping and this leads to uneven dosing of drug, to uneven blood levels of the drug characterized by peaks and valleys, and accordingly this does not provide controlled-rate therapy over an extended period of time. Presently, pentoxifylline is administered two or three times a day because pentoxifylline and pentoxifylline metabolites have short half-lives of 0.4 to 0.8 hours and 1.0 to 1.6 hours respectively. The prior art dosing patterns and the half-life characteristics of pentoxifylline dictate of the need for a dosage form that can administer pentoxifylline at a controlled rate over an extended time to provide continuous therapy and enhanced patient therapy. The drug pentoxifylline is known in *Physician's Desk Reference*, 47 Edition, 1993, pages 1125 to 1126, published by Medical Economics Data, Montvale, N.J.

The prior art provided a dosage form that can administer a drug for continuous therapy. For example, in U.S. Pat. No. 4,327,725 issued to Cortese and Theeuwes, and in U.S. Pat. Nos. 4,612,008; 4,765,989; and 4,783,337 issued to Wong, Barclay, Deters and Theeuwes a dosage form is disclosed that provides therapy affected by a high osmotic pressure generated inside the dosage form. The dosage form of these patients operate successfully for delivering a drug that develops a high osmotic pressure gradient across a semi-permeable membrane. The drug pentoxifylline however, possesses a low osmotic pressure of about 6 to 6.5 atmospheres, which dictates against providing an osmotic dosage form for use in the gastrointestinal tract. The gastrointestinal tract has a higher osmotic pressure environment, and this adversely affects the delivery of pentoxifylline from a dosage form in this environment.

It is immediately apparent in the light of the above presentation, that an urgent need exists for a dosage form endowed with physical-chemical properties for delivering pentoxifylline. The need exists for a dosage form for delivering pentoxifylline at a controlled-rate in a continuous dose in a therapeutic range while simultaneously providing the beneficial therapy. It will be appreciated by those versed in the drug dispensing art, that if such a dosage form is provided that can administer pentoxifylline in the desired delivery program, the dosage form would represent an advancement and a valuable contribution in the dispensing art.

OBJECT OF THE INVENTION

Accordingly, in view of the above presentation, it is an immediate object of this invention to provide a dosage form that delivers pentoxifylline in a continuous-release dose over time.

Another object of the present invention is to provide a dosage form for administering pentoxifylline at a controlled-rate in a therapeutic-dose over an extended period over time.

Another object of the present invention is to provide a dosage form that delivers pentoxifylline in the gastrointestinal tract, by a process selected from osmotic, diffusion, bioerosion or ion-exchange.

Another object of the invention is to provide pentoxifylline in a controlled-continuous-release dose to a patient for maintaining an essentially constant pentoxifylline level in the blood as a function of a prolonged-release system.

Another object of the invention is to provide a pentoxifylline continuous-release dosage form that provides a slow-release of pentoxifylline over an extended time.

Another object of the present invention is to provide a dosage form that substantially reduces and/or substantially eliminates the unwanted influence of a gastrointestinal environment on the delivery of pentoxifylline in the gastrointestinal tract.

Another object of the present invention is to provide an improvement in a dosage form that administers pentoxifylline, wherein the improvement comprises delivering the pentoxifylline in a continuous-release dose from the dosage form for predictable and improved therapy.

Another object of the invention is to provide a dosage form that delivers pentoxifylline orally to a patient in need of pentoxifylline therapy.

Another object of the present invention is to provide a dosage form that delivers by osmotic, diffusion, bioerosion or ion-exchange a therapeutic dose of pentoxifylline over an extended time for dosage form governed pentoxifylline therapy.

Another object of the invention is to provide a method for administering pentoxifylline by orally administering pentoxifylline in a dose per unit time over an extended time to a patient in need of pentoxifylline therapy.

Another object of the present invention is to provide a method for administering pentoxifylline in a therapeutic range while simultaneously substantially-avoiding a toxic range of the pentoxifylline.

Another object of the invention is to provide a method for administering pentoxifylline by administering a dosage form that administers by osmotic, diffusion, bioerosion or ion-exchange pentoxifylline as a dosage form governed rate over an extended time.

Another object of the present invention is to provide a therapeutic composition comprising pentoxifylline blended with a pentoxifylline pharmaceutically acceptable compatible carrier.

Other objects, features and advantages of the invention will be more apparent to those versed in the dispensing art from the accompanying detailed specification, taken in conjunction with the drawings and claims.

BRIEF DESCRIPTION OF THE DRAWINGS

In the drawing figures, which are not drawn to scale, but are set forth to illustrate various embodiments of the invention, the drawing figures are as follows:

Drawing

Drawing

Drawing

Drawing FIG. 4 depicts an instant-release coat comprising pentoxifylline on the exterior surface of the dosage form;

Drawing

In the drawings and in the specification, like parts on related figures are identified by like numbers. The terms appearing earlier in the specification and in the description of the drawings, as well as embodiments thereof are further described in the specification.

DETAILED DESCRIPTION OF THE DRAWINGS

Figure 1:
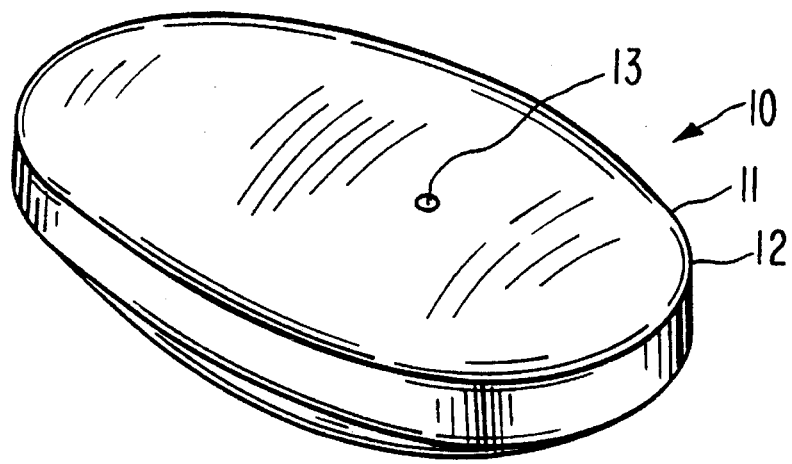
FIG. 1 is a general view of a dosage form designed and shaped for oral administration and delivery of pentoxifylline at a continuous-release rate over time to a patient in need of pentoxifylline therapy.

Turning now to the drawing figures in detail, which drawing figures are examples of dosage forms provided by this invention, and which examples are not to be construed as limiting, one example of a dosage form is seen in drawing FIG. 1. In drawing FIG. 1, a dosage form 10 is seen comprising a body member 11, which body member 11 comprises a wall 12 that surrounds and forms an internal area, not visible in drawing FIG. 1. Drawing FIG. 10 comprises at least one exit 13 that connects the exterior of dosage form 10 with the interior of dosage form 10. The dosage form 10 of drawing FIG. 1 illustrates a controlled-release dosage form that delivers pentoxifylline over an extended time. The dosage form comprising controlled-release properties provided by this invention is successful at maintaining substantially therapeutic pentoxifylline levels in the blood or in body tissue. The dosage form provided by this invention comprises continuous-release, extended-release and prolonged-release forms. These dosage forms provide pentoxifylline blood levels and targeted tissue levels within a therapeutic range optionally below side-effect levels over time. An extended period of time, as used for the purpose of this invention includes a prolonged period of time, and a continuous-controlled release period of time. The extended, prolonged and continuous time denotes a duration of pentoxifylline delivery time over that achieved by conventional drug delivery forms such as tablets and capsules.

Figure 2:
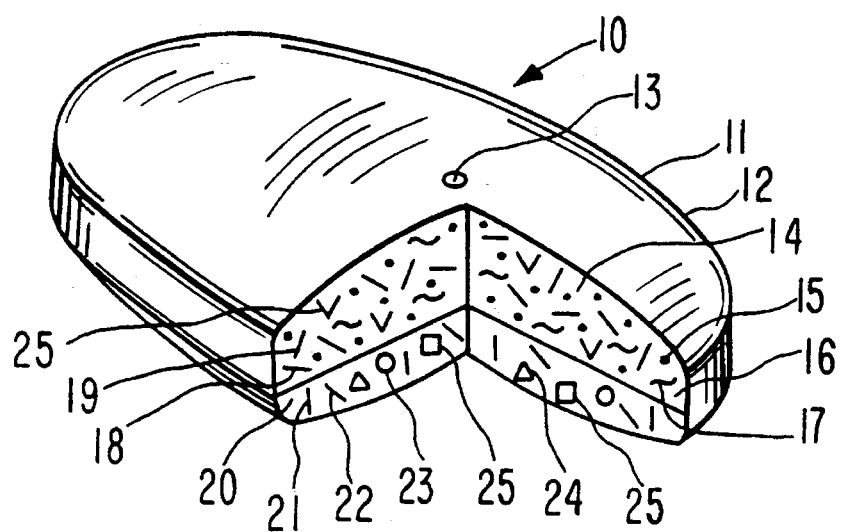
FIG. 2 is an opened view of drawing FIG. 1 for depicting one embodiment of the dosage form comprising a pharmaceutical composition comprising pentoxifylline and a displacement composition for urging the pharamecutical composition from the dosage form.

In drawing FIG. 2, dosage form 10 as seen in opened section. In drawing FIG. 2, dosage form 10 comprises a body 11, a wall 12 that surrounds and defines an internal compartment 14. Internal compartment 14 communicates through exit port 13 with the exterior of dosage form 10. Wall 12 of dosage form 10 comprises totally or in at least a part a composition that is permeable to the passage of an exterior fluid, such as an aqueous fluid or a biological fluid present in the gastrointestinal tract. Wall 12 is nontoxic and it is substantially impermeable to the passage of pentoxifylline 15 present in compartment 14. Wall 12 is substantially inert, it maintains its physical and chemical integrity during the dispensing line of pentoxifylline. The phrase, maintains its physical and chemical integrity means wall 12 does not lose its structure and it does not undergo chemical change during the dispensing of pentoxifylline.

Wall 12 comprises a composition that does not adversely effect an animal, a human, or components of the dosage form. Compositions for forming wall 12, are in one embodiment, a cellulose ester polymer, a cellulose ether polymer and a cellulose ester-ether polymer. These cellulosic polymers have a degree of substitution, D.S., on the anhydroglucose unit, from greater than 0 up to 3 inclusive. By degree of substitution is meant the average number of hydroxyl groups originally present on the anhydroglucose unit comprising the cellulose polymer that are replaced by a substituting group. Representative polymers include a member selected from the group consisting of cellulose acylate, cellulose diacylate, cellulose triacylate, cellulose acetate, cellulose diacetate, cellulose triacetate, mon-, di- and tricellulose alkanylates, mono-, di-, and tricellulose aroylates. Exemplary polymers include cellulose acetate having a D.S. up to 1 and an acetyl content up to 21%; cellulose acetate having a D.S. of 1 to 2 and an acetyl content of 21 to 35%; cellulose acetate having a D.S. of 2 to 3 and an acetyl content of 35 to 44.8%, and the like. More specific cellulosic polymers include cellulose propionate having a D.S. of 1.8 and a propyl content of 39.2 to 45% and a hydroxyl content of 2.8 to 5.4% cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7; cellulose tricylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentanoate, co-esters of cellulose such as cellulose acetate butyrate and cellulose acetate propionate.

Additional semipermeable polymers comprise acetaldehyde dimethyl cellulose acetate, cellulose acetate ethyl carbamate, cellulose acetate methyl carbamate, cellulose acetate diethyl aminoacetate; semipermeable polyamides; semipermeable polyurethanes; semipermeable sulfonated polystyrenes; semipermeable cross-linked selective polymers formed by the coprecipitation of a polyanion and polycation as disclosed in U.S. Pat. Nos. 3,173,876, 3,276, 586, 3,541,005; 3,541,006, and 3,546,142; semipermeable polymers as disclosed by Loeb and Sourirajan in U.S. Pat. No. 3,133,132; semipermeable lightly cross-linked polystyrene derivatives; semipermeable cross-linked poly(sodium styrene sulfonate); semipermeable cross-linked poly(vinylbenzyltrimethyl ammonium chloride); semipermeable polymers exhibiting a fluid permeability of $2.5 \times 10^{-8}$ to $2.5 \times 10^{31}$ 4(cm$^2$/hr.atm) expressed per atmosphere of hydrostatic or osmotic pressure difference across the semipermeable wall. The polymers are known to the art in U.S. Pat. Nos. 3,845,770; 3,916,899; and 4,160,020; and in *Handbook of Common Polymers* by Scott, J. R. and Roll, W. J., 1971 published by CRC Press, Cleveland, Ohio.

Compartment 14 comprises pentoxifylline 15 in a first layer 16. Pentoxifylline 15 is chemically 3,7-dihydro-3,7-dimethyl-1-(5-oxohexyl)- 1H-purine-2,6-dione as disclosed in *The Merck Index*, Eleventh Edition, page 1131, published 1989 in Rahway, N.J. Pentoxifylline is therapeutically indicated for improving the flow properties of blood by decreasing its viscosity. Pentoxifylline is used for treating chronic peripheral arterial disease, and this increases blood flow to the affected microcirculation and it enhances tissue oxygenation. Pentoxifylline undergoes a first-pass effect and its metabolites appear after pentoxifylline dosing in the plasma. The metabolites include 1-(5-hydroxyhexyl)-3,7-dimethylxanthine and 1-(3-carboxypropyl)-3,7-dimethylxanthine. The plasma half-life of pentoxifylline if from 0.4 to 0.8 hours and the plasma half-life of the metabolites is from 1 to 1.6 hours. Pentoxifylline is indicated for the treatment of patients with intermittent claudication on the bases of chronic occlusive disease. The medical use of pentoxifylline is disclosed in *Physicians' Desk Reference,* 47 Edition, pages 1125 to 1126, 1993). The amount of pentoxifylline 15 in dosage form 10 is 100 ng to 750 mg that is delivered over an extended period of up to 30 hours. Pentoxifylline 15 is present in dosage form 10 comprising individual dose of 5, 25, 50, 75, 100, 150, 250, 300, 400, 500 and 600 mg of pentoxifylline. Pentoxifylline is delivered by dosage form 10 over a period of immediate delivery of time up to 30 hours. Pentoxifylline is disclosed in *The Pharmacological Basis of Therapeutics*, Edited by Gilman and Rall, Eighth Edition, page 628, (1990), Pergamon Press.

Pentoxifylline 15 is present in layer 16 for delivering pentoxifylline 15 through exit port 13. Pentoxifylline layer 16 comprises 20 wt % to 85 wt % of pentoxifylline 15; 5 wt % to 75 wt % of a member selected from the group consisting of polyethylene oxide 17 possessing a 175,000 to 225,000 molecular weight and/or a polyethylene oxide possessing a 275,000 to 325,00 molecular weight; 0 wt % to 40 wt % of a member selected from the group consisting of a hydroxyproplyalkylcellulose 18, including hydroxypropylmethylcellulose, hydroxypropylethylcellulose, hydroxypropylisopropylcellulose, hydroxypropylbutylcellulose, hydroxypropylpentylcellulose and hydroxypropylhexylcellulose possessing a 9,200 to 240,000 molecular weight; 0 wt % to 15 wt % of a hydroxyalkylcellulose 19, including hydroxymethylcellulose, hydroxyethylcellulose, hydroxypropylcellulose, hydroxyisopropylcellulose and hydroxybutylcellulose possessing a 7,200 to 650,00 molecular weight; 0 wt % to 20 wt % polyvinyl pyrrolidone comprising a 20,000 to 50,000; 0 wt % to 5 wt % of a lubricant selected from the group consisting of magnesium stearate, calcium stearate, sodium stearate, potassium stearate and stearic acid; and 0 wt % to 25 wt % of an osmotically active compound 25. The total weight of all ingredients in layer 16 is equal to 100 wt %, wherein wt % denotes weight percent.

Compartment 14 comprises a displacement layer 20. Displacement layer 20 is a push layer that cooperates with layer 16 to achieve delivery of pentoxifylline 15 by pushing layer 16 from dosage form 10. Displacement layer 20 comprises 40 wt % to 99 wt % of a polyalkylene oxide 21 comprising a 3,000,000 to 7,500,000 molecular weight such as a polyethylene oxide; 0 wt % to 20 wt % of a microcrystalline cellulose 22 possessing a 15,000 to 60,000 molecular weight; 0 wt % to 15 wt % of a member selected from the group 23 consisting of hydroxypropylalkylcellulose, hydroxypropylmethylcellulose, hydroxypropylethylcellulose, hydroxypropylisopropylcellulose, hydroxypropylbutylcellulose and hydroxypropylpentylcellulose possessing a 9,200 to 275,000 molecular weight; 0 wt % to 20 wt % of a carboxypolymethylene polymer 24 comprising a 50,000 to 3,000,000 molecular weight which polymer is known also as carboxyvinylpolymer as described in U.S. Pat. Nos. 2,798,053; 2,909,462; 3,825,069 and 4,284,857; 0 wt % to 30 wt % to an osmotically active compound 25 comprising a member selected from the group consisting of an inorganic salt, organic salt, acid, ester, carbohydrate, oxide, magnesium sulfate, magnesium chloride, sodium chloride, lithium chloride, potassium chloride, potassium sulfate, sodium sulfate, sodium sulfite, lithium sulfate, potassium lactate, mannitol, urea, magnesium succinate, tartaric acid, raffinose, sorbitol, sucrose, fructose, and glucose. Displacement layer 20 comprises 0 wt % to 3 wt % of a lubricant such as a member selected from the group consisting of stearic acid, magnesium stearate, magnesium oleate, calcium stearate, calcium oleate, oleic acid, and caprylic acid; and 0 wt % to 3 wt % of ferric oxide; and 0 to 3 wt % of butylated hydroxytoluene (BHT), The polymers are known in U.S. Pat. Nos. 3,845,770 and 4,160,020; and in the *Handbook of Common Polymers* by Scott, J. R. and Roll, W. J., published by CRC Press, Cleveland, Ohio. The total wt % of all ingredients in displacement layer 20 equals 100 weight percent.

Figure 3:
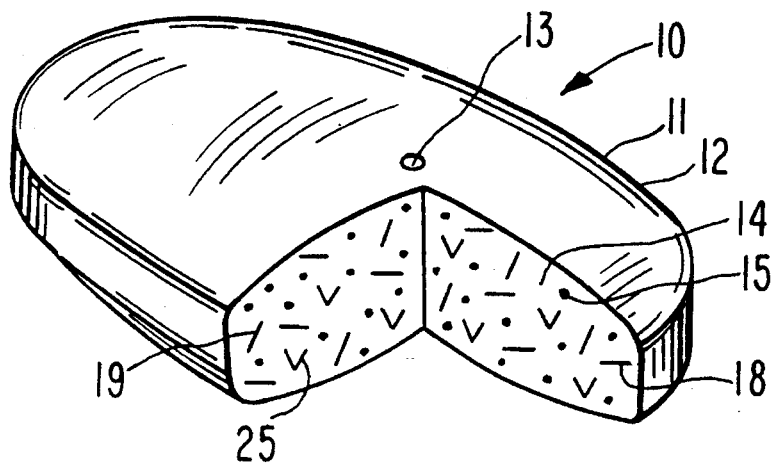
FIG. 3 is an opened view of drawing FIG. 1 depicting a different embodiment of the dosage form that comprises a single pharmaceutical composition comprising pentoxifylline and an osmotically active agent for aiding in the delivery of the pharmaceutical composition from the dosage form.

In drawing FIG. 3 dosage form 10 is seen in opened view. In drawing figure, dosage form 10 comprises body 11, wall 12, exit port 13 and internal compartment 14. Internal compartment comprises a single homogenous composition comprising 0 wt % to 55 wt % of pentoxifylline 15; from 5 wt % to 35 wt % of a member selected from the group consisting of a polyethylene oxide 17 comprising a 175,000 to 225,000 molecular weight, and a polyethylene oxide possessing 275,000 to 325,000 molecular weight, that is from 175,000 to 325,000 molecular weight; 0 wt % to 40 wt % of a cellulose ether 18 selected from the group consisting of hydroxypropylalkylcellulose, hydroxypropylmethylcellulose, hydroxypropylethylcellulose, hydroxypropylisopropylcellulose, hydroxypropylbutylcellulose, hydroxyopropylpentylcellulose, and hydroxypropylhexylcellulose possessing a 9,200 to 240,000 molecular weight; 0 wt % to 15 wt % of a hydroxyalkylcellulose 19, including a hydroxymethylcellulose, hydroxyethylcellulose, hydroxypropylcellulose, hydroxyisopropylcellulose and hydroxybutylcellulose possessing a 7,200 to 650,0000 molecular weight; 0 wt % to 25 wt % of an osmotically active compound 25; and 0 wt % to 5 wt % of a lubricant. The total weight of all ingredients in the single homogeneous core is equal to 100 wt %.

Figure 4:
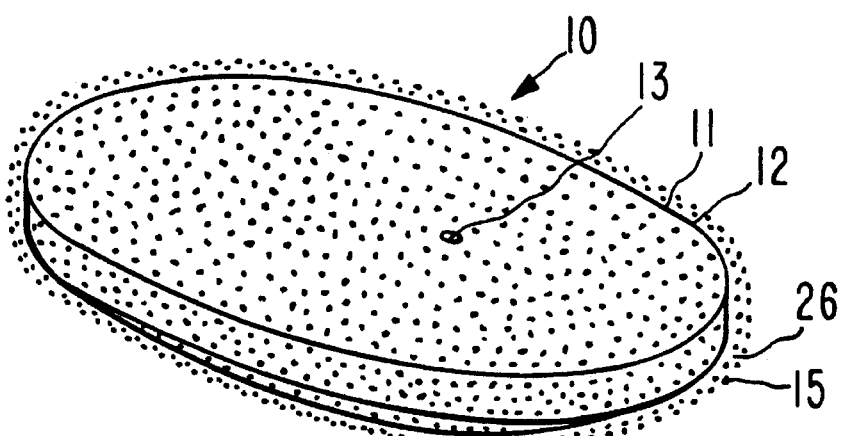
FIG. 4 is a view of the dosage form of drawing FIG. 1, which drawing

Dosage form 10, as seen in drawing FIG. 4 depicts another manufacture provided by the invention. Dosage form 10 comprises an external coat 26 on the exterior surface of dosage form 10. Coat 26 is a therapeutic composition comprising 1 mg to 150 mg of pentoxifylline 15, represented by dots 15. Exterior coat 26 provides pentoxifyllene 15 over one hour, blended with an aqueous-releasable carrier comprising a member selected from the group consisting of alkyl cellulose, methylcellulose, hydroxyalkylcellulose, hydroxypropylcellulose, hydroxypropylmethylcellulose, hydroxypropylethylcellulose, hydroxyalkylcellulose, and acacia. Coat 26 optionally comprises 0 to 5.5 wt % of polyethylene glycol or 0 to 5.5 wt % acetylated triglyceride. Coat 26 provides pentoxifyllene 15 therapy as coat 26 dissolves or undergoes dissolution in the presence of gastrointestinal fluid and concurrently therewith delivers pentoxifyllene 15 to a pentoxifylline receiving patient. Coat 26 provides pentoxifylline on entrance into the gastrointestinal tract for immediate pentoxifylline 15 therapy.

The dosage form 10, as used further for the purpose of this invention, includes also dosage forms that mediate the efficiency of therapeutic pentoxifylline by imparting improved therapy. The dosage forms 10 embraced by this invention improved patient acceptance and improved patient compliance for better therapy. The dosage forms 10 contemplated by the present invention comprises a dosage form 10 selected from the group consisting of bioerodible-mediated dosage form, diffusion-mediated dosage form, and ion-exchange-mediated dosage form.

The bioerodible-mediated dosage form 10 comprises a bioerodible polymer matrix containing pentoxifylline. This dosage form provides a bioerodible mediated-release rate of pentoxifylline delivered to a drug receptor as the polymer matrix at a rate of release controlled by the bioeroding matrix over time. The bioerodible polymers for forming the dosage form containing the pentoxifylline include poly(ester), poly(amine), poly(lactide), poly(glycolide), poly(lactide-co-glycolide), poly(caprolactone), poly(hydroxybutyric acid), poly(orthoester), poly(orthocarbonate), poly(acetate), poly(carbohydrate), poly(peptide), poly(acetal), and poly(dihydropyron).

The diffusion-mediated dosage form comprises membrane-controlled diffusion consisting of diffusion through a polymer membrane or diffusion through a porous-polymer. The diffusion mediated dosage form structurally includes a polymer matrix with pentoxifylline therein, that is released by the process of diffusion and, a reservoir or depot with pentoxifylline therein that is released therefrom by the process of diffusion through a contacting polymer rate-governing membrane. Representative polymers for providing a diffusional-dosage form comprise a member selected from the group consisting of poly(olefin), poly(vinyl), poly(carbohydrate), poly(peptide), poly(condensation), poly(rubber), and poly(silicone), polymers. Representative of specific polymers are a member selected from the group consisting of poly(ethylene), poly(propylene), copoly(ethylene-vinyl acetate), poly(isobutylethylene), poly(vinylacetate), cross-linked poly(vinyl alcohol), poly(methacrylate), poly(amide), poly(ester), and poly(silicone).

Dosage form 10 manufactured as an ion-exchange mediated dosage form comprises water-insoluble crosslinked polymers with pentoxifylline bound to the resin. In dosage form 10, pentoxifylline is released at a rate controlled by the pentoxifylline resin complex by the ionic environment within the gastrointestinal tract. The pentoxifylline attached to the resin are released at a rate controlled by the exchanging-rate with a charged ion in the gastrointestinal tract. The ion-exchange mediated dosage form comprises cation-exchange resins containing electronegative charges and anion-exchange resins containing electropositive charges. The cation-exchange resins include strong-acid or weak-acid resins as with sulfonic acid, carboxylic acid and phosphoric acid; and the anion-exchange resins include strong-base and weak-base resins as with quaternary ammonium, secondary amine, tertiary amine, aromatic and tertiary amine aliphatic resins. Examples include acidic ion-exchange resins such as Amberlite IR-120, basic ion-exchange resins such as Amberlite IRA-400, and weak basic ion-exchange resins such as Amberlite IR-45.

Dosage form 10, as further provided by this invention, and as seen in the above drawing figures can be manufactured for administering pentoxifylline 15 by the oral route. Dosage form 10 comprising exterior and interior pentoxifylline 15 can be sized and shaped for administering pentoxifylline 15 by the sublingual or the buccal routes. The sublingual and buccal routes can be used for quicker therapy and they can be used when a small dose of pentoxifylline 15 is needed for therapy. The buccal and sublingual routes can be used as a by-pass of the first pass of hepatic metabolism pentoxifylline 15. The sublingual or buccal routs can be used for administering the first dose of pentoxifylline 15 followed by permitting dosage form 10 entrance into the gastrointestinal tract for pentoxifylline 15 delivery.

PROCESS FOR PROVIDING DOSAGE FORM

Dosage form 10, when manufactured as an osmotic controlled-release dosage form comprises at least one passageway 13. The phrase controlled-release as used herein, indicates that control is exercised over both the duration and the profile of the pentoxifylline-release pattern. The expression passageway, as used for the purpose of this invention, includes aperture, orifice, bore, pore, porous element through which the pentoxifylline can be pumped, diffuse, travel or migrate, a hollow fiber, capillary tube, porous overlay, porous insert, microporous member, and porous composition. The expression also includes a compound that erodes or is leached from wall 12 in the fluid environment of use to produce at least one passageway 13 in dosage form 10. Representative compounds suitable for forming at least one passageway, or a multiplicity of passageways, includes an erodible poly(glycolic) acid or poly(lactic) acid member in the wall; a gelatinous filament; a water-removable poly(vinyl alcohol); leachable compounds such as fluid removable pore-forming polysaccharides, acid, salts, or oxides. A passageway or a plurality of passageways can be formed by leaching a compound such as sorbitol, sucrose, lactose, fructose, or the like, from the wall to provide a controlled-release dimensioned pore-passageway. The passageway can have any shape such as round, triangular, square, elliptical, and the like, for assisting in the controlled-metered release of pentoxifylline from dosage form 10. Dosage form 10 can be constructed with one or passageways in spaced apart relation to one or more surfaces of a dosage form 10. Passageway 13 and equipment for forming passageways are disclosed in U.S. Pat. Nos. 3,845,770 and 3,916,899 by Theeuwes and Higuchi; in U.S. Pat. No. 4,063,064 by Saunders et al.; and in U.S. Pat. No. 4,088,864 by Theeuwes et al. Passageways comprising controlled releasing dimension, sized, shaped and adapted as a releasing-pore formed by aqueous leaching to provide a releasing-pore of controlled release-rate are disclosed in U.S. Pat. No. 4,200,098 by Ayer and Theeuwes; and in U.S. Pat. No. 4,285,987 by Ayer and Theeuwes.

Wall 12 is manufactured in one process, comprises an air suspension process. This procedure consists in suspending and tumbling a compressed drug core comprising a single layer or a bilayer core, in a current of air and wall forming composition until a wall is applied to the drug-push compartment. The air suspension procedure is well-suited for independently forming the wall. The air suspension procedure is described in U.S. Pat. No. 2,799,241; *J. Am. Pharm.*

Assoc., Volume 48, pages 451 to 454, (1959); and ibid, Volume 49, pages 82 to 84, (1960). Dosage form 10 can be coated also with a wall-forming composition in a Wurster® air suspension coater, using methylene dichloride-methanol cosolvent, for example, 80:20, wt:wt, an ethanol-water, or acetone-water cosolvent, for example, 95:5 wt:wt using 2.5 to 4% solids. An Aeromatic® air suspension coater using a methylene dichloride-methanol cosolvent for example, 80:20 wt:wt, can be used for applying wall 12. Other wall forming techniques such as a pan-coating system, wherein wall forming compositions are deposited by successive spraying of the composition on the drug-core compartment, accompanied by tumbling in a rotating pan. Finally, the wall coated compartments are dried in a forced air over at 30° C. to 50° C. for up to a week to free dosage form 10 of solvent. Generally, the walls formed by these techniques have a thickness of 1 to 30 mils (with a presently preferred thickness of 4 to 10 mils).

Dosage form 10 of the invention is manufactured by standard manufacturing techniques. For example, in one manufacture the drug and other core-forming ingredients comprising a single drug layer or bilayer core facing the exit means 13 are blended and pressed into a solid layer, or a solid bilayer. The drug and other ingredients can be dry-blended or blended with a solvent and mixed into a solid or semisolid formed by conventional methods such as ball-milling, calendaring, stirring, roll-milling or churning and then pressed into a preselected shape. The layer possesses dimensions that correspond to the internal dimensions of the area the layer is to occupy in the dosage form and in a bilayer it also possesses dimensions corresponding to the second layer for forming a contacting arrangement therewith. Next, in a bilayer core, the push layer is placed in contact with the drug layer. The push layer is manufactured using techniques for providing the drug layer. The layering of the drug layer and the push layer can be fabricated by convention press-layering techniques. Finally, a single layer or the two layer compartment forming members are surrounded and coated with an outer wall. A passageway is laser, leached, or mechanically drilled through the wall to contact the drug layer. When the passageway is formed by a laser, the dosage form is optically-oriented automatically by the laser equipment for forming the passageway on the preselected surface for forming the passageway.

In another manufacture, dosage form 10 is manufactured by the wet granulation technique. In the wet granulation technique, for example, the drug and the ingredients comprising the drug-forming layer are blended using a solvent, such as ethyl alcohol-water 98:2 v:v (volume:volume) as the granulation fluid. Other granulating fluid, such as denatured alcohol 100%, can be used for this purpose. The ingredients forming the drug layer are individually passed through a 20 mesh screen and then thoroughly blended in a mixer. Next, other ingredients comprising the drug layer are dissolved in a portion of the granulation fluid, such as the cosolvent described above. Then, the latter prepared wet blend is slowly added to the drug blend with continual mixing in the blender. The granulating fluid is added until a wet blend is produced, which wet mass then is forced through a 20 mesh screen onto oven trays. The blend is dried for 18 to 24 hours at 30° C. to 50° C. The dry granules are sized then with a 20 mesh screen. Next, a lubricant is passed through screen, such as an 80-mesh screen, and added to the dry screen granule blend. The granulation is placed in a blender and blended for 1 to 15 minutes. A push layer is made by the same wet granulation techniques. The compositions are pressed into their individual layers in a Manesty® layer press.

Another manufacturing process that can be used for providing the compartment-forming composition layers comprises blending the powdered ingredients for each layer independently in a fluid bed granulator. After the powdered are dry blended in the granulator, a granulating fluid, for example, poly(vinyl-pyrrolidone) in water, or in denatured alcohol, or in 95:5 ethyl alcohol/water, or blends of ethanol and water, is sprayed on the powders. Optionally, the ingredients can be dissolved or suspended in the granulating fluid. The coated powders are then dried in a granulator. This process granulates all the ingredients present therein while added the granulating fluid. After the granules are dried, a lubricant such as stearic acid or magnesium stearate is added to the granulator. The granules for each separate layer are pressed then in the manner described above.

Dosage form 10 of the invention can be manufactured by mixing a drug with composition-forming ingredients and pressing the composition into a layer possessing dimensions that correspond to the internal dimensions of the compartment of the dosage form. In another manufacture the drug and other drug composition-forming ingredients and a solvent are mixed into a solid, or a semisolid, by conventional methods such as ballmilling, shaking, calendaring, tumbling, stirring or rollmilling, and then pressed into a preselected layer-forming shape. Next, a layer of a composition comprising an osmopolymer and an optional osmagent are placed in contact the drug layer. The layering of the first layer comprising the drug and the second layer comprising the osmopolymer and optional osmagent composition can be accomplished by using a conventional layer press technique. The wall can be applied by molding, brushing, spraying or dipping the pressed bilayer's shapes with wall-forming materials. Another and preferred technique that can be used for applying the wall is the air-suspension coating procedure. This procedure consists in suspending and tumbling the two contacting layers in current of air until the wall-forming composition surrounds the layers. The air suspension procedure is described in U.S. Pat. No. 2,799,241; *J. Am. Pharm. Assoc.*, Vol. 48 pp 451–454 (1979); and, abid, Vol. 49, pp 82–84 (1960). Other standard manufacturing procedures are described in *Modern Plastics Encyclopedia*, Vol. 46, pp 62–70 (1969); and in *Pharmaceutical Science*, by Remington, 14th Ed., pp 1626–1678 (1970), published by Mack Publishing Co., Easton, Pa.

Exemplary solvents suitable for manufacturing the wall, a single layer and a bilayer core include inert inorganic and organic solvents final laminated wall. The solvents broadly include members selected for the group consisting of aqueous solvents, alcohols, ketones, esthers, ethers, aliphatic hydrocarbons, halogenated solvents, cyclaliphatics, aromatics, hetercyclic solvents and mixtures thereof. Typical solvents include acetone, diacetone, alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane ethylene glycol monoethyl ether, ethylene glycol monoethyl acetate, methylene dichloride, ethylene dichloride, propylene dichloride, carbon tetrachloride, chloroform, nitroethane, nitropropane, tetrachoroethan, ethyl ether, isopropyl ether, cyclohexane, cyclooctane, benzene, toluene, naptha, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

DETAILED DISCLOSURE OF EXAMPLES OF THE INVENTION

The following examples are merely illustrative of the present invention and they should not be considered as limiting the scope of the invention in any way as these examples and other equivalents thereof will become apparent to those versed in the art in the light of the present disclosure, the drawings and accompanying claims.

EXAMPLE 1

A dosage form is designed and adapted for delivering pentoxifylline as an orally active hemorheological drug for the treatment of peripheral vascular disease by increasing regional microcirculation is provided according to the following examples. A dosage form is designed to delivery pentoxifylline as expressed by the following physical mathematical equation 1:

$$Z = K(A/h)\Delta\pi S \qquad 1$$

wherein, Z is the zero-order release rate of the dosage form, wherein Z is expressed in mg/hr; K is the permeability of a semipermeable wall that surround a core comprising pentoxifylline, wherein K is cm$^3$ ml/hr atm; A is the area of the semipermeable wall, wherein A equals cm$^2$; h is the thickness of the semipermeable wall, expressed in mil or mm wherein mil equals 0.001 inch and h equals 0.0254 mm/mil; $\Delta\pi$ is the osmotic pressure difference between the core comprising pentoxifylline and the environment of use, with $\pi$ equal to atm; and S is the pentoxifylline concentration from the effluent of the dosage form, wherein S equals mg/ml.

The physical properties of pentoxifylline are set forth in accompanying Table 1 and Table 2. In Table 1, $S_d$ (mg/ml) denotes the solubility of pentoxifylline in water, artificial gastric fluid and artificial intestinal fluid, $\pi$ (atm) is the osmotic pressure difference between pentoxifylline and the environment consisting of water, artificial gastric fluid and artificial intestinal fluid, and $\pi S_d$ (mg/ml $\pi$ atm) is the osmotic pressure of pentoxifylline of a saturated pentoxifylline solution at 37° C. In Table 1, pentoxifylline is present free of other components.

TABLE 1

| Medium | $S_d$ (mg/ml) | $\pi$ (atm) | $\pi S_d$ (mg/ml $\pi$ atm) |
|---|---|---|---|
| H$_2$O | 190 | 6.5 | 1,235 |
| AGF (pH = 1.2) | 187 | — | — |
| AIF (pH = 7.5) | 151 | 6.5 | 982 |

Table 2 sets forth the properties of pentoxifylline in the presence of other compounds, wherein PVP denotes poly(vinylpyrrolidone), and PEG denotes polyethylene glycol with a 3350 average molecular weight.

TABLE 2

| Medium | $S_d$ (mg/ml) | $\pi$ (atm) | $\pi S_d$ (mg/ml $\pi$ atm) |
|---|---|---|---|
| 20% PVP in H$_2$O | 127 | 11.4 | 1,448 |
| 10% PEG 3350 | 158 | 9.0 | 1,422 |
| 20% PEG 3350 | 131 | 14.4 | 1,886 |

Accompanying Table 3 depicts the mutual solubility of pentoxifylline in potassium chloride solutions at 37° C.

TABLE 3

| $C_{KCl}$ (mg/ml) | $S_d$ (mg/ml) | $\pi$ (atm) | $\pi S_d$ (atm $\pi$ mg/ml) |
|---|---|---|---|
| 283 | 6 | 211 | 1.3 (10)$^3$ |
| 152 | 23 | 94 | 2.2 (10)$^3$ |
| 79 | 54 | 50 | 2.8 (10)$^3$ |
| 0 | 192 | 6.5 | 1.3 (10)$^3$ |

Figure 5:
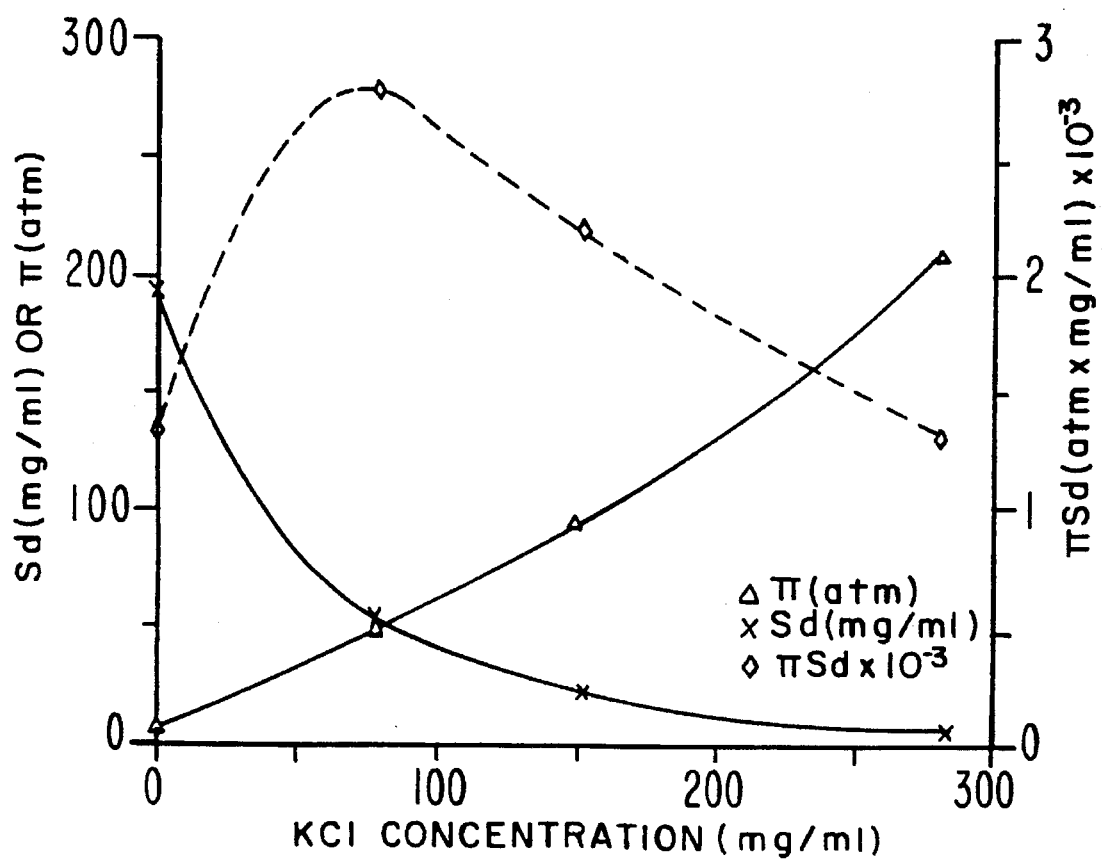
FIG. 5 is a graph that illustrates the solubility of pentoxifylline and potassium chloride solution; and, Drawing

The above tables depict pentoxifylline in an osmotic dosage form would exhibit a solubility dependence of pH variations of the gastrointestinal tract. The tables indicate a saturation solution of pentoxifylline exhibits a low osmotic pressure of 6.5 atm. The data indicates pentoxifylline alone cannot function in an osmotic dosage form as the osmotic pressure of the gastrointestinal tract is about 8 atm. Accompanying drawing FIG. 5, the broken lines connected by diamonds represents the product of the osmotic pressure of pentoxifylline times the solubility of pentoxifylline in the presence of varied concentrations of osmotic agent KCl, the curve with triangles represents the osmotic pressure vs concentration of potassium chloride at 37° C., and the line with X represents the solubility of pentoxifylline in the presence of varied concentrations of KCl.

Next a dosage form for delivering pentoxifylline is prepared as follows: first, 70 wt % pentoxifylline; 22 wt % 300,000 molecular weight polyethylene oxide; 5 wt % 200,000 molecular weight polyethylene oxide; and 3 wt % and 11,200 molecular weight hydroxypropylmethylcellulose are passed through a 40 mesh screen. Then, the mixture is dry blended in a V-blender and transferred to a Hobart mixer. Next, anhydrous denatured alcohol is added slowly to the mixer's bowl to produce a wet mass. The wet mass is passed through a 20 mesh screen and then air dried. The dried mass is passed through a 20 mesh screen to produce a composition comprising pentoxifylline, polyethylene oxide, and hydroxypropylmethylcellulose granules. Then, 0.25 wt % magnesium stearate is added to the granules Next, a displacement composition comprising 68.75 wt % polyethylene oxide possessing a 7,000,000 molecular weight, 5 wt % carboxyvinyl polymer, a water-soluble polymer of acrylic acid crosslinked with 1% of a polyalkylether of sucrose having an average of 5.8 alkyl groups for each molecule of sucrose possessing a 3,000,000 molecular weight, 20 wt % sodium chloride, 5 wt % hydroxypropylmethylcellulose possessing a 11,200 molecular weight, and 1 wt % ferric oxide are dry blended in a V-blender for 7 to 10 minutes and then transferred to a mixer. Then, anhydrous, denatured alcohol is added to the mixer operating at low speed. When most of the drug mixture had aggregated, the mixer is run at higher speed until the aggregate clumps are broken to smaller, screenable wet granules. The wet granules are passed through a 20 mesh screen and allowed to air dry, and then rescreened through the 20 mesh screen. Then, 0.25 wt % magnesium stearate is added to the dry granules, reblended and rescreened to yield displacement granules. The pentoxifylline composition prepared above, and the displacement composition are bilayered tableted with a press using a ¾ inch (19 mm) oval tool, to yield a bilayer core.

Next, a semipermeable wall is coated around the core. The composition for forming the semipermeable wall comprises 60 wt % cellulose acetate comprising a 39.8% acetyl content, and 40 wt %. The solvents used for coating the core consisted of 80% acetone and 20% methane (wt:wt). The cores are coated in a 12 inch (305 mm) pan. The final wall coated cores are dried for 18 hours at 45° in a light current of air. An exit passageway was drilled through the semipermeable wall connecting the pentoxifylline with the exterior of the dosage form. The exit port had a diameter of 30 mils (0.76 mm). The dosage form exhibited a pentoxifylline mean release rate of 22.89 mg/hr.

EXAMPLE 2

The procedure in Example 1 is followed with all conditions as set-forth, except in Example 2, the drug layer comprises 70 wt % pentoxifylline, 26 wt % polyethylene oxide possessing a 200,000 molecular weight, and 3.75 wt % hydroxypropylmethylcellulose possessing a 9,200 molecular weight; and 0.25% magnesium stearate and a displacement layer comprises 83.68 wt % polyethylene oxide possessing a 7,500,000 molecular weight, 10 wt % carboxyvinyl polymer possessing a 3,000,000 molecular weight, and 5 wt % hydroxypropylmethylcellulose possessing a 9,200 molecular weight and 0.25% magnesium stearate, 1 wt % ferric oxide and 0.08 wt % butylated hydroxytoluene. The dosage form provided by this example had a pentoxifylline mean release rate of 38.54 mg/hr.

EXAMPLE 3

The procedure of Example 1 is followed in this example, for providing a pentoxifylline layer comprising 70 wt %, of pentoxifylline, and 30 wt % of polyethylene oxide possessing a 200,000 molecular weight; a displacement layer comprising 51.60 wt % polyethylene oxide possessing a 7,500,00 molecular weight, 25 wt % of microcrystalline cellulose, 15 wt % sodium chloride, 3.75 wt % hydroxypropylmethylcellulose possessing a 11,200 molecular weight, 3.75 wt % of carboxyvinyl polymer, 0.75 wt % ferric oxide and 0.15 wt % magnesium stearate; and a semipermeable wall comprising 60 wt % cellulose acetate, 20 wt % hydroxypropylcellulose, and 20 wt % polyethylene glycol; with a release rate of 23.21 mg/hr. over 24 hours.

EXAMPLE 4

Same as Example 1 except the push layer excipients were dry mixed in a blender and directly compressed in a layered arrangement.

EXAMPLE 5

A dosage form is provided according to the above examples, wherein the dosage form of this example is characterized by an exterior pentoxifylline coat on the exterior surface of the dosage form. The exterior coat comprises 1 mg to 150 mg of pentoxifylline and 1 mg to 150 mg of hydroxypropylmethylcellulose having a 9,200 to 175,00 molecular weight. The coat is applied from a solvent consisting of methylene chloride and ethanol. The exterior coated dosage forms are dried on stainless steel trays at 50° C. for 48 hours. The dosage form, in a fluid environment such as the gastrointestinal tract, release the coat from the semipermeable wall in from 1 minute to 60 minutes at 37° C.

EXAMPLE 6

A dosage form is provided according to the above examples, wherein the dosage form of this example is characterized by an exterior pentoxifylline coat on the exterior surface of the dosage form. The exterior coat comprises 1 to 150 mg of pentoxifylline and 1 mg to 150 mg of a hydroxypropylcellulose, comprising a 7,500 to 125,000 molecular weight. The coat is applied from a solvent consisting of methylene chloride and ethanol. The exterior coated dosage forms are dried on stainless steel trays at 50° C. for 48 hours. The dosage form, in a fluid environment such as the gastrointestinal tract, release the coated pentoxifylline from the semipermeable wall in from 1 minute to 60 minutes at 37° C.

EXAMPLE 7

A continuous-release dosage form is provided by the inventors for the continuous delivery of pentoxifylline at 1 mg/hr to 50 mg/hr over an extended period of 24 hours, by following the examples of 1 to 5. The dosage form is administered according to the method of the invention for providing pentoxifylline therapy on a patient in need of pentoxifylline therapy.

EXAMPLE 8

A bioerodible dosage form is prepared by mixing into poly(2,2-dioxo-trans-1,4-cyclohexane dimethylene tetrahydrofuran is heated in a laboratory Teflon® flat coated pan equipped with a surface thermometer to about 150° C. and then 125 mg of pentoxifylline is added to the polymer. Next, the pentoxifylline and bioerodible poly(orthoester) are thoroughly mixed to produce a good dispersion of the pentoxifylline. After the pan cooled to room temperature, the polymer-pentoxifylline is removed from the pan and a solid film of tablet shape is pressed at 250° F. (121.1° C.), and at 10,000 psi for 5 minutes to yield an oral dosage form. The dosage form is prepared under an essentially dry, inert atmosphere using oven dried apparatus. The dosage form surface bioerodes in the gastrointestinal tract at a dosage-controlled rate and at an extended rate over prolonged period of time.

EXAMPLE 9

A diffusional-releasing dosage form is prepared by mixing 33 parts by weight of pentoxifylline with 67 parts of medical grade room temperature polydimethyl siloxane. The resulting liquid mixture is molded into an oval shaped form, and surrounded with molecularly, biaxially oriented, heat shrinkable polyethylene film of 2 mm thickness with heat for 3 seconds at 300° F. resulting in the film effecting a tight and intimate contacting film with the depot pentoxifylline, that release pentoxifylline over an extended time.

EXAMPLE 10

A dosage form adapted, designed and shaped as an osmotic drug delivery device is manufactured as follows: first, 5656 grams of pentoxifylline, poly(ethylene oxide) possessing a 200,000 molecular weight are added to a Freund Flow-Coater's® bowl, a fluid bed granulator. The bowl was attached and granulation process was initiated. Next, the dry powders were air suspended and mixed for 7 minutes. Then a solution prepared by dissolving 240 g of poly(vinylpyrrolidone) identified as K29-32 having an average molecular weight of 40,000, in 760 g of water was sprayed from nozzles onto the powder. The coating conditions were monitored during the process of aqueous poly(vinylpyrrolidone) as follows: solution spray rate of 125 g/min from each nozzle for a total spray rate of 250 g/min: inlet temperature 45° C.; and process air flow of 1000 cfm.

The coating process was computerized and automated in cycles. Each cycle contained 30 seconds of solution spraying followed by two seconds of drying and 10 seconds of filter bags shaking to unglue and possible power deposits. At the end of the solution spraying, the coated granulated particles were continued with the drying process for 25 minutes. The machine was turned off, and the coated granules were moved from the Flo-Coater. The coated granules were sized using a Fluid Air Mill. The granulation was transferred to a Rotocone®, mixed and lubricated with magnesium stearate and mixed with butylated hydroxytoluene.

Next, a push composition is prepared as follows: first, 950 g of pharmaceutically acceptable poly(ethylene oxide) comprising a 5,000,000 molecular weight, 36.7 g and 10 g of ferric oxide separately are screened through a 40 mesh screen. Than all the materials were transferred to Hobart mixer and mixed for 5 minutes. 400 ml of denatured ethyl alcohol was added to the mixed powders in the Hobart bowl and mixing was continued for 2 minutes. The mixed mall was then passed through a 10 mesh screen and allowed to dry at room temperature for 16 hours and again passed through a 20 mesh screen. The screened granulation was mixed with 2.5 g magnesium stearate in a rollermill for 5 minutes.

Next, the pentoxifylline drug composition and the push composition are compressed into bilayered tablets. First, 857 mg of the tandospirone composition is added to a punch and tamped, then 196 mg of the push composition is added and the layers are pressed under a pressure head of two tons into a ¾" (1.91 cm) contacting layered arrangement.

The bilayered arrangements are coated with a semipermeable wall. The wall forming composition comprises 60% cellulose acetate having a 39.8% acetyl content, and 40% hydroxypropyl cellulose having a molecular weight of 18,500. The wall-forming composition is dissolved in an acetone:methanol (80:20) wt:wt) cosolvent to make a 4% solids solution. The wall forming composition is sprayed onto and around the bilayers in a 24" Vector® HiCoater.

Figure 6:
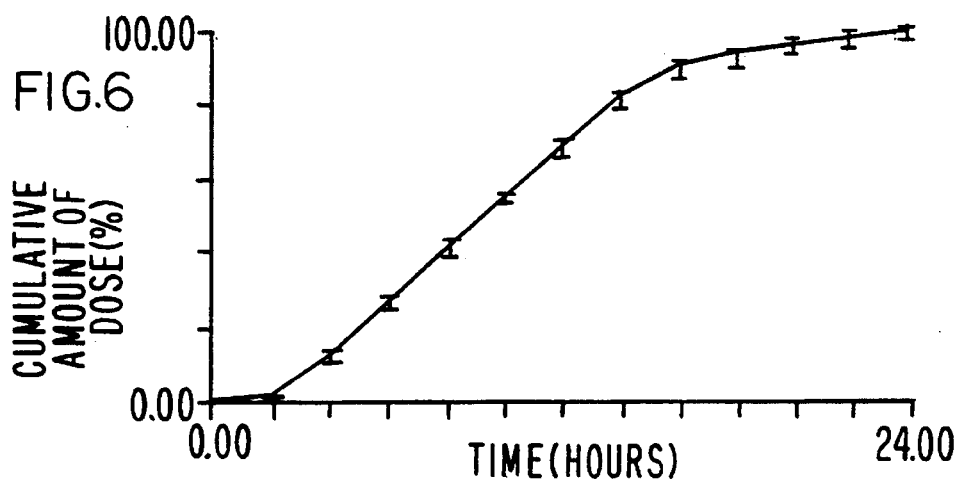
FIGS. 6 to 8 depict pentoxifylline release patterns provided by the inventors.

Next, two 25 mil (0.635 mm) exit passageways are mechanically drilled through the semipermeable wall to connect the drug layer with the exterior of the dosage system. The residual solvent is removed by drying for 48 hours at 50° C. and 50% humidity. Next, the osmotic systems are dried for 1 hour at 50° C. to remove excess moisture. The dosage form produced by this manufacture provides 70 wt % pentoxifylline, 26 wt % poly(ethylene oxide) possessing a 200,000 molecular weight, 3 wt % poly(vinyl pyrrolidone) possessing a 40,000 molecular weight, 0.25 wt % magnesium stearate, and 0.08 wt % butyl hydroxytoluene. The push composition comprises 95 wt % poly(ethylene oxide) comprising a 5,000,000 molecular weight, 3.67 wt % hydroxypropylmethylcellulose possessing 11,200,000 molecular weight, 1.0 wt % ferric oxide and 0.25 wt % magnesium stearate. The semipermeable wall comprises 60 wt % cellulose acetate comprising a 39.8% acetyl content, and 40 wt % Klucel ER comprising a molecular weight. The dosage form comprises two passageways, 25 mils (0.635 mm), and it had a pentoxifylline mean release rate of 39.73 mg/hr. Accompanying FIG. 6 depicts the cumulative delivery pattern for a dosage form provided by this example.

EXAMPLE 11

Following the procedure of Example 9, all conditions were as set forth except that the expansion layer comprised the following composition:

| | |
|---|---|
| 83.68 wt % | poly(ethylene oxide) PEO 7,000.000 molecular weight |
| 10.00 wt % | carbomer 934P, NF |
| 5.00 wt % | hydroxypropylmethylcellulose, 2910 USP 5 cps |
| 1.00 wt % | ferric oxide |
| 0.25 wt % | magnesium stearate |
| 0.08 wt % | butytene hydroxtoluene (BHT) |

Figure 7:
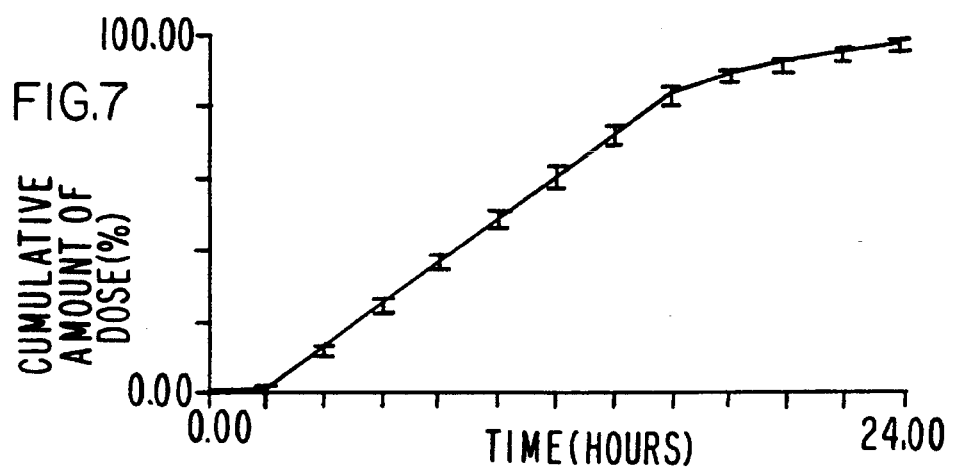

Accompanying drawing FIG. 7 depicts the cumulative release pattern of this example.

EXAMPLE 12

Figure 8:
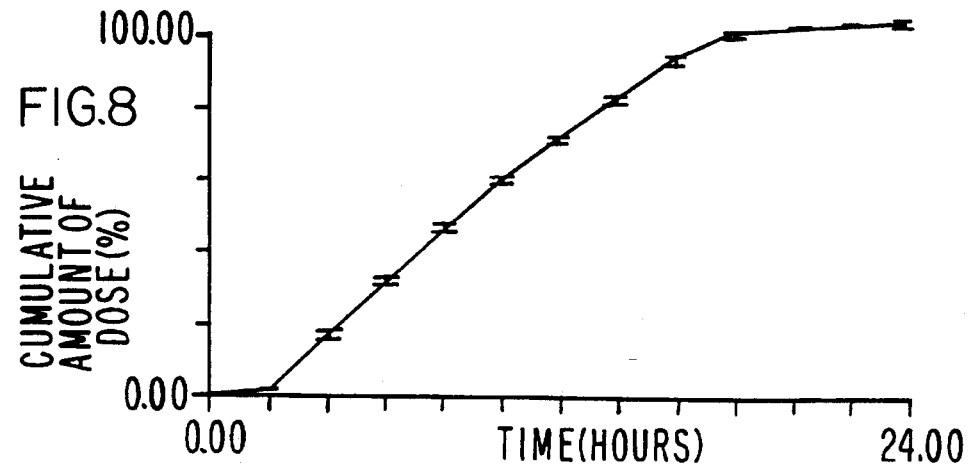

The procedure of Example 9 was followed with all conditions as set forth except the excipients were dry mixed into a blend and directly comprised on a layered arrangement. The cumulative release pattern is depicted in accompanying drawing FIG. 8.

Method of Practicing the Invention

One method to practice the invention pertains to a method for delivery pentoxifylline to a patient in need of a hemorheological pentoxifylline. The method comprises (A) admitting orally into the patient a dosage form comprising means for delivering pentoxifylline, where the dosage form comprises: (1) a wall that surrounds and forms an internal compartment, said wall comprising a semipermeable composition permeable to the passage of fluid and impermeable to the passage of pentoxifylline; (2) a pentoxifylline composition in the compartment that forms a dispensable pentoxifylline composition when the dosage form is in use and an external fluid fluxes through the semipermeable wall; (3) an orifice in the dosage form delivers the pentoxifylline from the dosage form: (B) imbibing fluid through the wall at a rate determined by the osmotic pressure gradient across the wall thereby causing the pentoxifylline composition to become dispensable; and, (C) delivering the pentoxifylline to the patient at a continuous rate over 24 hours.

The method comprises also admitting orally into a human a dosage form comprising 100 ng to 750 mg of pentoxifylline and 100 ng to 500 mg of a bioerodible polymer that releases the pentoxifylline by bioerosion at a rate controlled by bioerosion over an extended period up to 30 hours. The method comprises further admitting into a patient in need of pentoxifylline therapy a dosage form comprising a diffusion-governing polymer means that releases pentoxifylline by diffusion over an extended time.

The dosage form can be used in a buccal environment and in a sublingual environment, for delivering pentoxifylline for increasing red blood cell deformity, for reducing blood viscosity, and for decreasing the potential for platelet aggregation and thrombus formation. The dosage form administers up to 750 mg of pentoxifylline from the dosage form by a pentoxifylline releasing process selected from the group consisting of osmotic, diffusion, erosion, and fluid teaching from the dosage form over 24 hours to provide pentoxifylline therapy to the patient needing same.

The novel dosage form of this invention uses dual means for attainment of precise release rate of pentoxifylline to a patient for continuous-regulated pentoxifylline, while simultaneously maintaining the integrity and the character of the of the system. While there has been described and pointed out features and advantages of the invention, as applied to pentoxifylline, those skilled in the dispensing art will appreciate the various modifications, changes, additions and omissions in the system illustrated and described can be made out departing from the spirit of the invention.

We claim:

1. A dosage form for delivering pentoxifylline to a patient, the dosage form comprising:

(a) a wall comprising a semipermeable composition permeable to the passage of fluid and substantially impermeable to the passage of pentoxifylline;

(b) a compartment defined by the wall;

(c) 10 ng to 750 mg of pentoxifylline in the compartment;

(d) an exit in the dosage form for the continuous release of pentoxifylline at a rate of 1 ng/hr to 30 mg/hr over an extended time of 24 hrs.

2. A dosage form for the continuous delivery of pentoxifylline to a patient, wherein the dosage form comprises:

(a) a wall comprising a semipermeable composition permeable to the flux of fluid and substantially impermeable to the flux of pentoxifylline;

(b) a compartment defined by the wall;

(c) a pentoxifylline layer in the compartment comprising 100 ng to 750 mg of pentoxifylline;

(d) a displacement layer in the compartment for the continuous-displacement of pentoxifylline from the dosage form; and release of pentoxifylline at a rate of 1 ng/hr to 30 mg/hr over an extended time of 24 hrs;

(e) an exit in the dosage form for the continuous-release of pentoxifylline over time.

3. A method for administering pentoxifylline to a patient in need of pentoxifylline, wherein the method comprises admitting into the patient a bioerodible-medicated dosage form comprising 100 ng to 750 mg of pentoxifylline in a bioerodible matrix that is continuously-administered at a rate of 1 ng/hr to 30 mg/hr controlled by the bioeroding matrix over an extended time up to 24 hours.

4. A method for administering pentoxifylline to a patient, wherein the method comprises:

(a) admitting into the patient a dosage form comprising:
  (1) a pentoxifylline composition comprising 100 ng to 750 mg of pentoxifylline;
  (2) a semipermeable wall that surrounds the pentoxifylline composition;
  (3) exit means in the dosage form for delivering pentoxifylline from the dosage form;

(b) imbibing fluid into the dosage form causing the pentoxifylline composition to become deliverable from the dosage form; and thereby, (c) administering the pentoxifylline at a continuous-rate of 1 ng to 50 mg per hour to the patient for pentoxifylline therapy.

5. A method for administering pentoxifylline to a patient, where in the method comprises:

(a) admitting into the patient a dosage form comprising:
  (1) a pentoxifylline composition comprising 100 ng to 750 mg of pentoxifylline;
  (2) a displacement composition that imbibes fluid and expands;
  (3) a semipermeable wall that surrounds (1) and (2);
  (4) an exit in the dosage form that connects the exterior of the dosage form with the pentoxifylline composition;

(b) imbibing fluid into the dosage causing the displacement composition to expand and cooperate with the pentoxifylline composition for delivering the pentoxifylline composition through the exit; and thereby (c) administering pentoxifylline to the patient for producing pentoxifylline therapy.

6. The method for administering pentoxifylline to a patient according to claim 5, wherein the pentoxifylline is administered for providing the hemorheological treatment of peripheral vascular disease, for increasing red blood cell deformity, for reducing blood viscosity, for decreasing platelet aggregation and decreasing thrombus formation.

7. A method for administering pentoxifylline to a patient in need of pentoxifylline therapy, wherein the method comprises admitting orally into the patient a diffusion-mediated dosage form comprising up to 750 mg of pentoxifylline that is administered by a pentoxifylline releasing diffusion polymers at a sustained and controlled rate of 1 ng/hr to 30 mg/hr over 24 hours to provide the patient with pentoxifylline therapy.

* * * * *